United States Patent [19]
Weiss

[11] Patent Number: 6,068,378
[45] Date of Patent: May 30, 2000

[54] EYE SELF-TEST DEVICE

[76] Inventor: Jeffrey N. Weiss, Northwest Medical Plaza, 5800 Colonial Dr., Suite 300, Margate, Fla. 33063

[21] Appl. No.: 09/245,481

[22] Filed: Feb. 5, 1999

Related U.S. Application Data

[60] Provisional application No. 60/110,736, Dec. 3, 1998.

[51] Int. Cl.[7] .......................................... A61B 3/02
[52] U.S. Cl. ............................................... 351/223
[58] Field of Search .................... 351/200, 222, 351/223, 224, 227, 237, 239, 243; 248/309.4

[56] References Cited

U.S. PATENT DOCUMENTS

| | | | |
|---|---|---|---|
| 5,646,710 | 7/1997 | Caskey | 351/223 |
| 5,838,422 | 11/1998 | Caskey | 351/223 |

*Primary Examiner*—George Manuel
*Attorney, Agent, or Firm*—Malin, Haley & DiMaggio, P.A.

[57] ABSTRACT

The novel design of the eye self-test device increases patient compliance by reminding the patient to self-test and allows the patient's doctor to monitor compliance with the testing regimen. The data may be recorded and the patient notified if a change in vision necessitates examination by the doctor. The test is robustly manufactured to withstand breakage and is lightweight and portable. Its preferred method of attachment is such that it is capable of adhering to any vertically visible surfaces such that the conspicuous location of the test should encourage an improvement in testing compliance. Patient information, including instructions for testing and the doctor's name and telephone number for contacting in case of emergency may be provided internal or external to the device.

19 Claims, 3 Drawing Sheets

EYE SELF-TEST DEVICE

This application claims the benefit of U.S. Provisional Application No. 60/110,736, filed Dec. 3, 1998.

This invention was disclosed in the Disclosure Documents Program of the U.S. Patent and Trademark Office on Jun. 1, 1998, Disclosure Document No. 436870.

BACKGROUND OF THE INVENTION

1. Field of the Invention

This invention relates to medical diagnostic methods, and, in particular, to a method for improving the compliance and reliability of patient self-testing the central field of vision. The device is set for test recording in one day or another interval and notifies the patient to self-test if it is not activated within the preset interval. A play-back counter or tracker indicates whether the patient has been complying with the testing schedule. The patient may be notified when a predetermined change from the normal test or baseline test is detected and is instructed to contact their physician.

2. Description of Related Art

The macula is a small area within the retina of the eye that allows us to see small details clearly. If a person loses macula function they experience a blur or a blank spot in the center of their vision. There are many diseases that affect the macula. The early detection of macular changes may result in successful treatment that may prevent or delay the loss of vision. Unfortunately, once the patient notices the loss of vision it may already be too late to treat the condition and prevent or reverse the loss of vision.

In order to monitor the health of the macula, patients are frequently given a grid of lines with a central spot. They are instructed to self-test their vision with the grid at a set interval, generally once a day or every other day and contact their eye doctor if they notice a bending or absence of the lines or change in vision. The manner in which the test is altered may also provide clues to diagnosis. Unfortunately, many patients forget to use the test and discard or lose it over the course of time. As a result, many patients that might have presented to their doctor early enough to have their vision saved lose their central vision unnecessarily. The early detection of a change in vision will become even more important as newer treatments for macular diseases become available.

It is therefore, to the effective resolution of the aforementioned problems and shortcomings that the present invention is directed.

Accordingly, it is an object of this invention to provide an eye test where the patient can determine changes from normal.

It is another object of this invention to provide, by its configuration and method of attachment, a small, lightweight and portable device with stable adherence to a surface such that the test may be placed in a location that is conspicuously visible to the patient and will not be lost or accidentally discarded. The device is surrounded by a hard case to minimize breakage.

It is still another object of this invention to provide a timer that is preset for the patient's self-testing. If the patient does not self-test within the designated period of time, a sound or light is activated at preset times and duration to remind the patient to self-test.

It is yet another object of this invention to provide the patient's doctor's name, address and telephone number such that this information is readily available in case of emergency.

It is a further object of this invention to provide a long-lasting internal battery or rechargeable power supply for the device to obviate the need for frequent battery changes.

It is a further object of this invention to provide a device that records patient compliance with the preset testing frequency and that may be examined by the eye doctor to determine patient compliance.

It is yet another object of this invention to provide a device that notifies the patient when a preset deviation from normal occurs. The notification would encourage the patient to contact the eye doctor for examination.

It is a further object of this invention to provide a device that contains a transmitter or a port for attachment to a telephone line for monitoring by a monitoring station, an intelligent docking station or to a computer that would alert the patient when a significant change in the test occurred and would instruct the patient to promptly contact their eye doctor.

BRIEF SUMMARY OF THE INVENTION

The foregoing objects are achieved and the foregoing problems are solved in one illustrative embodiment of the invention in which a grid is attached to a case containing electronics such that once the device is activated the patient self-tests according to a preset testing frequency. The device is lightweight and contains magnets and/or an adhesive for easy attachment to a vertically conspicuous location in which the test would be prominently displayed. The case contains a place for the eye doctor's business card or a label containing the eye doctors name and contact information or other information. If the patient does not self-test, a sound or light is activated at preset times and for a preset interval to encourage the patient to self-test. The eye doctor may play-back the number of patient self-tests to determine the patient's compliance. The patient may draw the deviations from normal on the grid and when a preset deviation from normal occurs the patient would be notified to promptly contact the doctor. The notification may consist of a sound or light generated by the device or external notification by a monitoring station, intelligent docking station, computer, eye doctor or other source.

It is estimated that in the preferred embodiment, the squares on the grid can be 4 mm in size. The grid and central fixation spot can be black on a white background and the grid test can be approximately 8 cm by 8 cm in size. The single grid test can be attached to a case approximately 9 cm in width and 10 cm in length. The test is to be performed with one eye at a time under a moderate light intensity while wearing the correct refraction for reading at approximately a 14 inch distance. However, these dimensions and criteria are not considered limiting and other ranges and values are considered within the scope of this invention.

The illustrated embodiment describes a device for detecting irregularities in the central 20 degrees of vision. It will be apparent to those skilled in the art that a similar patient compliance and monitoring methodology may be used for other self-testing devices including reading vision, glare or color vision.

In a first embodiment of the present invention the grid is made of paper, plastic or another material that may or may not record images. In a second embodiment the chart is displayed on a screen. In a third embodiment a port is provided for computer and/or telephone access. In a fourth embodiment one grid is displayed for one eye and a second is displayed for the second eye. The patient presses one button when self-testing. In a fifth embodiment the patient presses a button for performing the test with one eye and a second button for performing the test on the second eye.

In accordance with these and other objects which will become apparent hereinafter, the instant invention will now be described with particular reference to the accompanying drawings.

DETAILED DESCRIPTION OF THE INVENTION

Figures 1A, 1B:
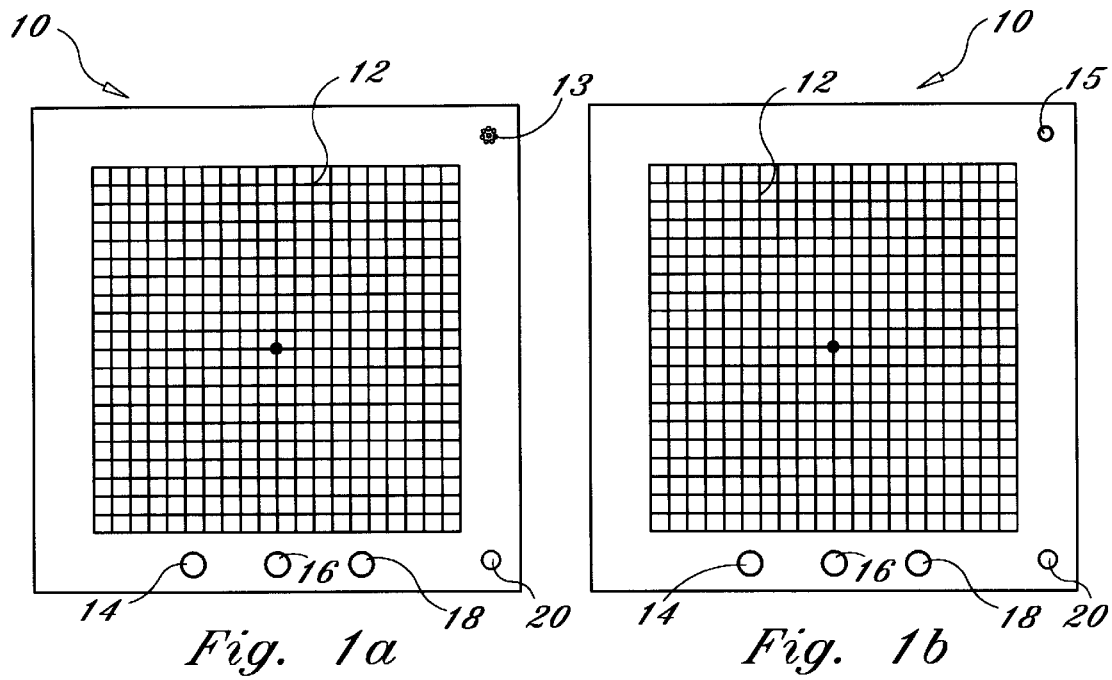
FIG. 1a is a front view of the present invention, and also illustrates an optional speaker member.
FIG. 1b is a front view of the present invention, and also illustrates an optional lighting element.
Figure 2:
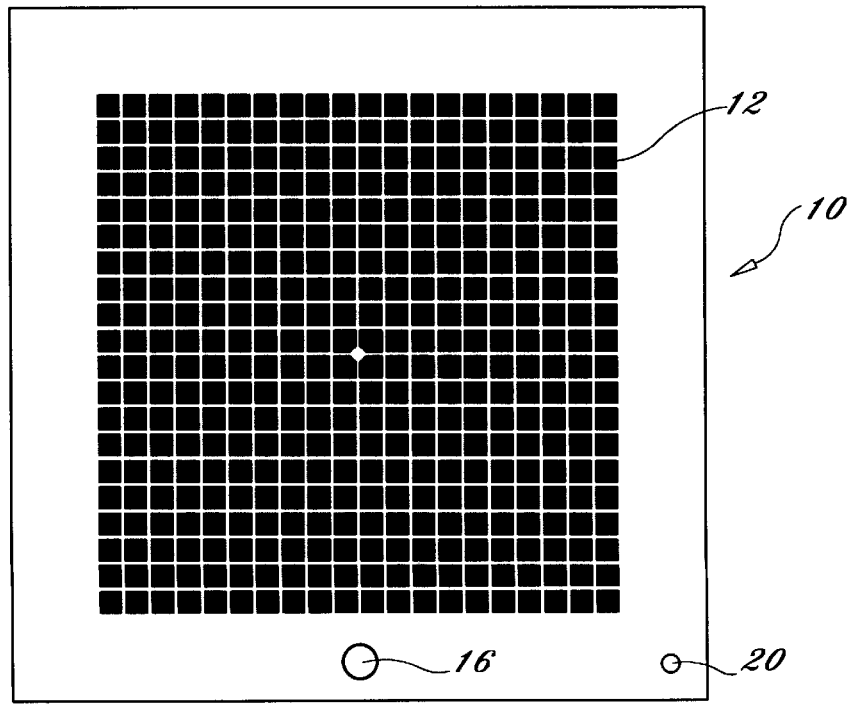
FIG. 2 is a front view of the present invention, illustrating an alternative background for the chart or grid.

As seen in FIG. 1a or 1b a first embodiment of the eye self test in accordance with the present invention is shown and generally designated test 10. Eye self test 10 includes a grid or chart 12, having a plurality of boxes and a central fixation spot. The lines and fixation spot may be dark on a light background (FIG. 1a or 1b) or alternatively light on a dark background (FIG. 2). Eye self test 10, including grid 12 may be made from a material that may or may not be written on, such as paper, plastic, and other conventional materials. If the surface is writable then the material may allow permanent recording or erasing. A recording instrument, such as a conventional pen or pencil, may be included.

Eye test 10 provides an alarm to the user, such as audio indicator (speaker) 13 (FIG. 1a) and/or visual indicator (light) 15 (FIG. 1b). The alarm indicates that it is time to administer a self-examination. In order to conserve battery life the device is first activated by pressing a button. Alternatively, the battery may be rechargeable. The device is then programmed for test recording in one, two or three day or another interval, preferably by pressing one of the buttons 14, 16 or 18 which are in communication with the circuitry or microprocessor of eye test 10. Alternatively, a three position switch 62 can be provided an in communication with the circuitry or microprocessor of eye test 10. The user merely sets switch 62 to the desired interval. Switch 62 can be provided at the back of eye test 10 (FIG. 4) or any other location on eye test 10. Other intervals, not shown, can be provided and are considered within the scope of the invention. Additionally, a single button, such as button 16 (FIG. 2), can be used, with the user pressing on the button for different time periods or a specific amount of successive times to indicate which time interval is desired.

When performing the test, the patient presses a button 20. The device acknowledges the self-test with a sound or light or other means and increases the test taken count. An additional button push within the same testing interval is not recorded by the device. If the test is not taken within the preset testing interval, the device will notify the patient through a sound, light, telephone call or other means.

In one embodiment, the device will activate a beeping sound five times at five second intervals at noon, 3 pm, 5 pm and at 7 pm on the missed day. By depressing a button, such as button 20, in a known fashion and in a known frequency and duration, the eye doctor will, by light, sound, a counter or tracker, or other determination devices, both internal and external to the device, determine the compliance of the patient to the self-testing schedule.

Figure 3:
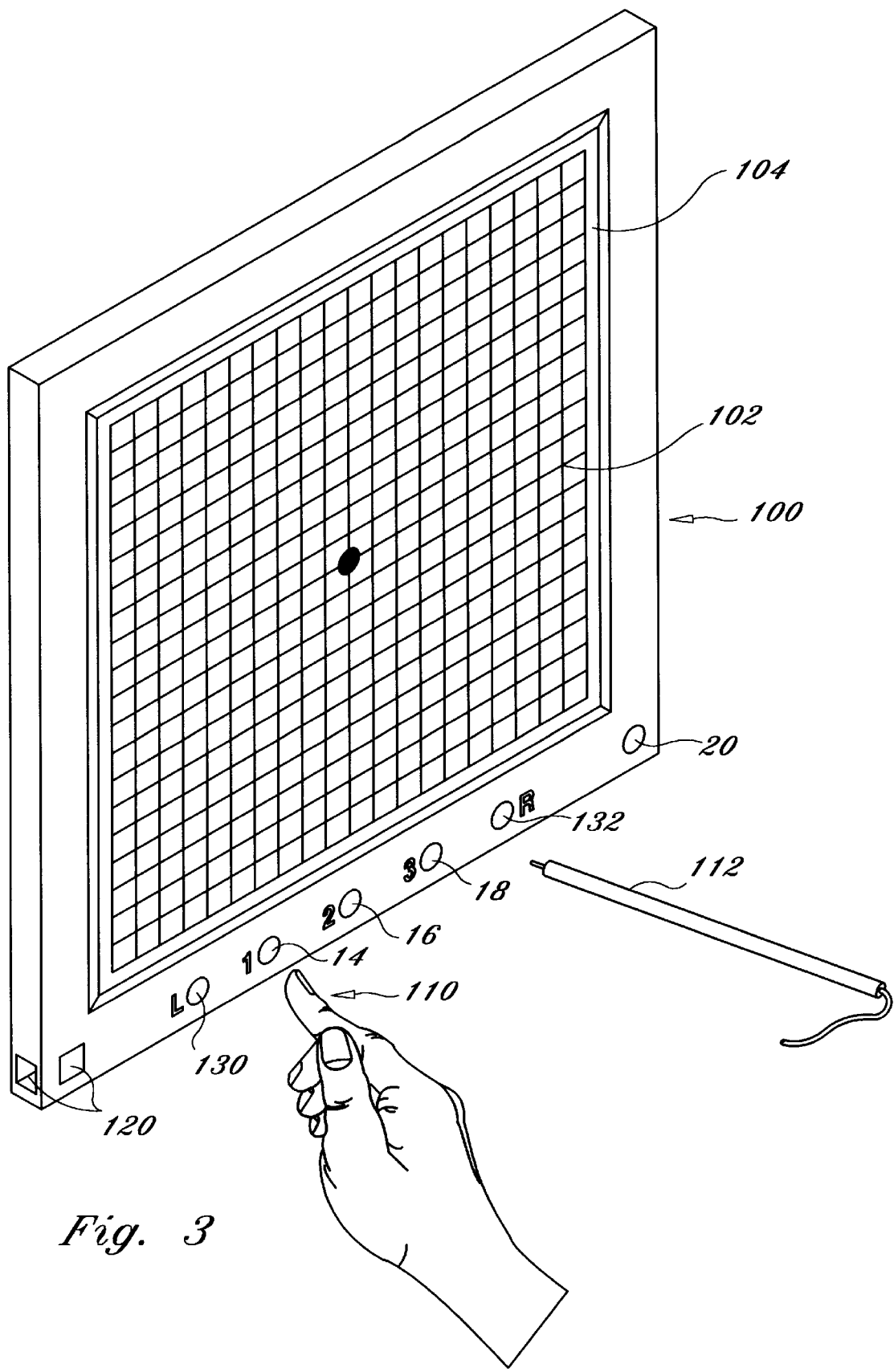
FIG. 3 is a perspective view of an alternative embodiment of the present invention in which the chart or grid is displayed on a screen.

An alternative embodiment of the present invention is generally designed test 100 and includes a similar grid 102 which is displayed on a screen member 104 (FIG. 3). The patient may record changes on the grid using his or her finger 110 or alternatively an included conventional recording marker 112 and the initial changes from normal are recorded. Significant variations in the test recording from normal or from the baseline test, as determined by internal software would notify the patient that the eye doctor should be contacted. Alternatively, a conventional transmitter may be provided, with test 100, such that external analysis of the test recording and notification of the patient may be provided by a computer, monitoring station, external docking station, eye doctor, or other source.

A conventional computer port and/or conventional telephone port 120 can be provided with test 10 or 100. If a significant variation in the test recording is determined by internal or external software, then the patient may be notified by the doctor, a monitoring company, or other means.

Additionally, a resettable audible, visual, digital and/or mechanical indicator, not shown, can be provided and will be in communication with the test taking counter or tracker of eye test 10 or 100. The counter or tracker, or similar device, records patient compliance with the preset testing frequency and can be examined by the eye doctor to determine patient compliance. The indicator would quickly inform the doctor of the amount of times the patient has administered the test since the last time the doctor reviewed eye test 10 or 100. A button or other conventional mechanism could be provided to reset the indicator back to zero.

Two separate tests 10 or 100, one for the left eye (FIG. 1a or 2), and one for the right eye (FIG. 1b or 2), can also be utilized and is considered within the scope of the present invention. The patient may push one button, when self-testing both eyes. In another embodiment (FIG. 3), one computerized grid is provided, using conventional technology. In this embodiment, information for each eye is programmed. When the patient pushes left eye button 130, information for the patient's left eye is retrieved by the computer, to allow the user to test his or her left eye. When the patient pushes right eye button 132, information for the patient's right eye is retrieved by the computer, to allow the user to test his or her right eye.

Figure 4:
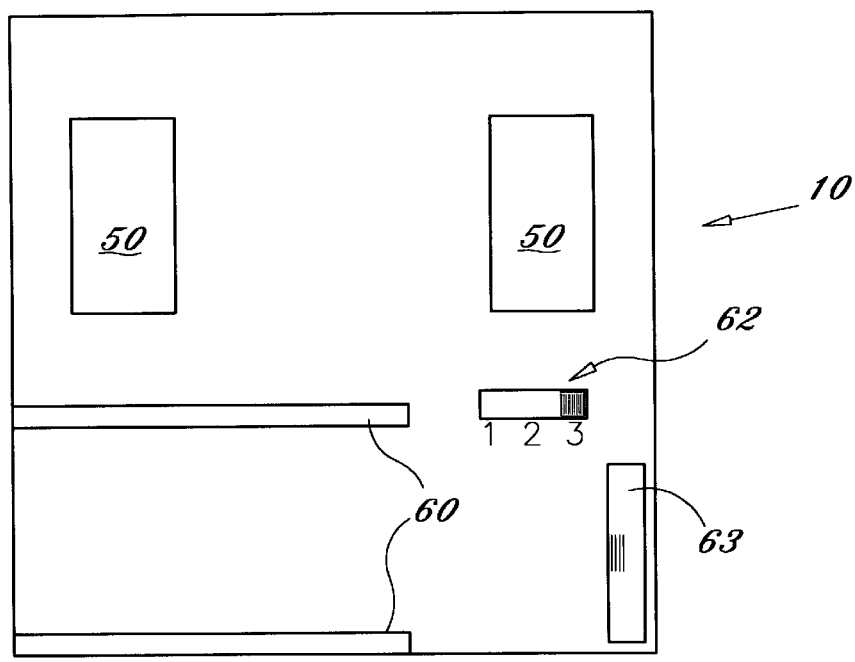
FIG. 4 is a back view of the present invention.
Figure 5:
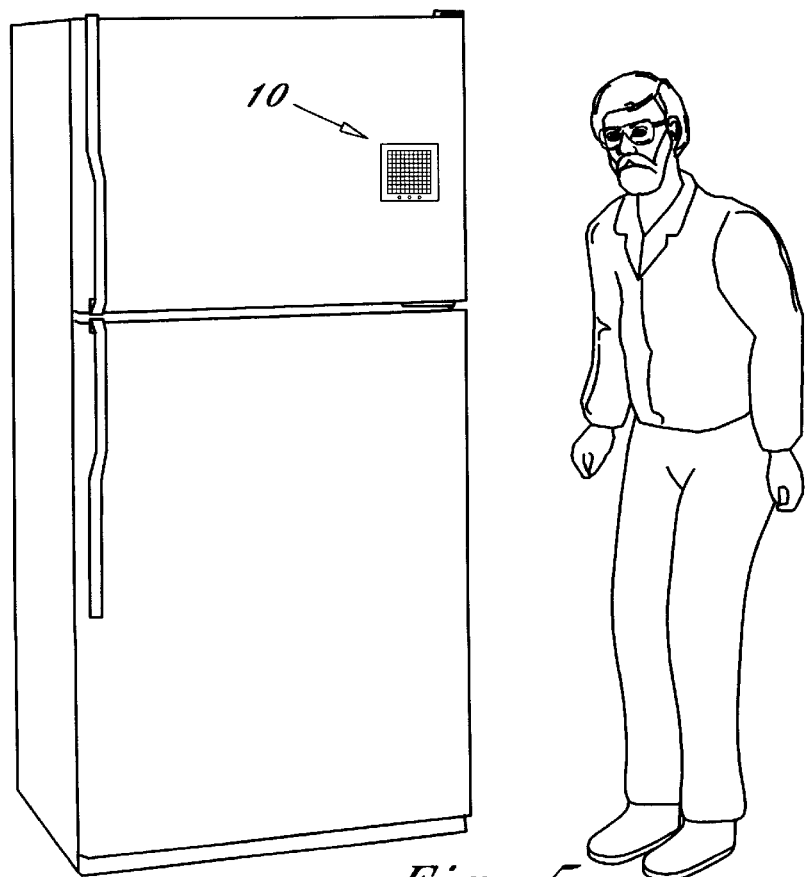
FIG. 5 is a perspective view of the present invention illustrating an individual using the present invention which is attached to the outer surface of a conventional refrigerator.

FIG. 4 illustrates the back surface of either eye test 10 or 100. One or more magnets 50 and/or another permanent or removable adhesive or attachment device is used to attach test 10 or 100 to a visible surface. FIG. 4 also illustrates battery compartment 63 which is provided when a battery (not shown) is used to power device 10 or 100. Alternatively, and in lieu of a battery, a rechargeable power supply can be used and is also considered within the scope of the invention. The lightweight nature of the device 10 or 100 allows it to be attached to a vertical surface. Retaining ledges 60 can be provided for storing a doctor's card, instructions for performing the test and/or other relevant information. FIG. 5 illustrates an individual using test 10 or 100 which is attached to the outer surface of a conventional refrigerator.

Test 10 and 100 uses conventional electrical and computer technology for programming and operational purposes, and is not limited to any one specific analog or digital embodiment. Furthermore, conventional software can be used for instructing the computer and microprocessor. Accordingly, any known electronic devices, chips, circuitry, components, hardware/software can be used to achieve the functions of the invention and are considered within the scope of the invention.

It is apparent to those skilled in the art that if the recording of the patient's test changes are desired, then one preferred embodiment is to use a test containing two grids. Alternatively, a computerized screen may display within a single grid size format the patient's recorded responses from each eye, and other information including a normal test, the instruction for performing the test and the doctor's name, address and telephone number for contacting in case of emergency. Though the invention is preferably used with a vertical surface, it should be recognized that the invention can also be used on a horizontal or diagonal surface and such uses are also within the scope of the invention.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An eye self test comprising:
   a body member having a self examination area;
   means for attaching said body member to a surface; and
   means for informing a user that it is time to perform an eye self test.

2. The eye self test of claim 1 wherein said examination area includes a grid.

3. The eye self test of claim 1 further including means for entering a testing interval period.

4. The eye self test of claim 3 wherein said means for entering allows for selection of a testing interval period of one day, two days, three days or longer.

5. The eye self test of claim 3 further including means for acknowledging that a user is taking a self test.

6. The eye self test of claim 1 wherein said means for informing is an audible sound.

7. The eye self test of claim 1 wherein said means for informing is an illumination member.

8. The eye self test of claim 1 further including means for recording any changes in a user's vision, discovered during user self examination.

9. The eye self test of claim 8 wherein said means for recording is a marker or finger.

10. The eye self test of claim 1 wherein said means for attaching is at least one magnet associated with a back surface of said body member.

11. The eye self test of claim 1 further including means for holding doctor information or any other relevant information.

12. The eye self test of claim 1 further including means for storing information necessary for testing a user's left eye and a user's right eye.

13. The eye self test of claim 12 further including means for setting said eye self-test for left eye testing or right eye testing and distinguishing between said left eye testing and said right eye testing.

14. An eye self test comprising:
   a body member having a self examination area;
   means for attaching said body member to a surface;
   means for entering a testing interval period;
   means for acknowledging that a user is taking a self test; and
   a test taken determinator, wherein activating said means for acknowledging incremently increases said test taken determinator.

15. The eye self test of claim 14 further including means for preventing any increase to said test taken determinator during an entered testing interval period when a user activates said means for acknowledging more than once during the entered testing interval period.

16. An eye self test comprising:
   a body member having a self examination area;
   means for attaching said body member to a surface; and
   means for recording and transmitting examination data to a remote area.

17. An eye self test comprising:
   a body member having a self examination area including a grid;
   means for entering a testing interval period of one day, two days, three days or longer;
   means for acknowledging that a user is taking a self test;
   means for indicating that said means for acknowledging has not been activated during an entered testing interval period;
   means for recording and transmitting examination data to a remote area; and
   means for attaching said body member to a surface.

18. The eye self test of claim 17 further including means for storing information necessary for testing a user's left eye and a user's right eye; and means for setting said self examination area for left eye testing or right eye testing.

19. An eye self test comprising:
   a body member having a self examination area including a grid;
   means for entering a testing interval period of one day, two days, three days or longer;
   means for acknowledging that a user is taking a self test;
   means for indicating that said means for acknowledging has not been activated during an entered testing interval period;
   means for recording and transmitting examination data to a remote area;
   means for storing information necessary for testing a user's left eye and a user's right eye;
   means for setting said self examination area for left eye testing or right eye testing;
   a test taken determinator, wherein activating said means for acknowledging incremently increases said test taken determinator;
   means for preventing any increase to said test taken determinator during an entered testing interval period when a user activates said means for acknowledging more than once during the entered testing interval period;
   means for checking the amount of times a user administered the eye test for a specific period; and
   means for removably attaching said body member to a vertical surface.

* * * * *